United States Patent [19]

Chen

[11] 4,090,989
[45] * May 23, 1978

[54] PROCESS FOR IMPROVING OZONE AND FLEX RESISTANCE OF CERTAIN ELASTOMERS

[75] Inventor: Mark Chaoming Chen, Wilmington, Del.

[73] Assignee: E. I. Du Pont de Nemours and Company, Wilmington, Del.

[*] Notice: The portion of the term of this patent subsequent to Mar. 7, 1995, has been disclaimed.

[21] Appl. No.: 698,018

[22] Filed: Jun. 21, 1976

[51] Int. Cl.$^2$ ............... C08K 5/52; C08L 7/00; C08L 47/00
[52] U.S. Cl. ............... 260/5; 260/45.7 P; 260/45.7 PH; 260/890; 260/956; 260/963; 260/967
[58] Field of Search ............... 260/5, 45.7 P, 45.7 PH, 260/890, 956, 963, 967

[56] References Cited

U.S. PATENT DOCUMENTS

| 2,767,206 | 10/1956 | Whetstone | 260/956 |
| 2,853,471 | 9/1958 | Beadell | 260/45.7 P |
| 3,172,871 | 3/1965 | Malz et al. | 260/45.7 PH |
| 3,562,210 | 2/1971 | Cassar et al. | 260/45.7 PH |
| 3,563,947 | 2/1971 | Gruber | 260/45.85 |
| 3,784,651 | 1/1974 | Inamoto et al. | 260/956 |

*Primary Examiner*—Donald E. Czaja
*Assistant Examiner*—H. H. Fletcher

[57] ABSTRACT

Ozone resistance of vulcanized chloroprene homopolymers and copolymers, chlorinated isobutylene/isoprene copolymers, and blends of any of the above with up to equal weight of styrene/butadiene copolymer or natural rubber is improved by incorporating into the polymer or polymer blend prior to vulcanization about 0.5–5 parts per 100 parts by weight of polymer or polymer blend of one or more of bis(5-norbornene-2-methyl) phosphite, tris(5-norbornene-2-methyl) phosphite, and tris(5-norbornene-2-methyl) phosphate. These esters also improve the flex resistance of chloroprene copolymers with sulfur and their blends with styrene-butadiene copolymers or natural rubber. In addition to improving ozone and flex resistance of the above polymers and polymer blends, these esters do not cause staining or discoloration of the vulcanized polymers.

19 Claims, No Drawings

PROCESS FOR IMPROVING OZONE AND FLEX RESISTANCE OF CERTAIN ELASTOMERS

BACKGROUND OF THE INVENTION

This invention relates to a process for improving the ozone resistance of certain vulcanized polymers and polymer blends, and in some cases also their flex resistance, as well as to polymers and polymer blends having improved ozone resistance and sometimes also flex resistance.

Elastomeric chloroprene polymer vulcanizates are quite resistant to ozone at normal temperature but are more readily degraded at elevated temperatures, especially when flexed or stretched. Other polymer vulcunizates are less resistant to ozone than chloroprene polymer vulcanizates. Various antiozonants are commercially available and usually are incorporated in such polymer formulations. While many such additives provide a good degree of protection against ozone deterioration, certain commercial antiozonants cause premature curing of polymer stocks, while most cause discoloration or staining of the polymer vulcanizates. There presently appears to be only one nonstaining antiozonant commercially available.

U.S. Pat. No. 3,563,947 (to W. F. Gruber) discloses the use of certain norbornene derivates as antiozonants for elastomeric chloroprene polymers. The copending allowed application Ser. No. 534,200 of M. C. Chen describes certain triarylphosphines which improve the flex resistance of chloroprene-sulfur copolymers.

SUMMARY OF THE INVENTION

According to the present invention, there is now provided a process for improving the ozone resistance of the following polymers and polymer blends in their vulcanized state:

A. chloroprene polymers containing about 90–100 weight percent chloroprene and 0–10 weight percent of a copolymerizable organic monomer.

B. chloroprene/sulfur copolymers in which the organic monomer composition is about 90–100 weight percent chloroprene and 0–10 weight percent of a copolymerizable monomer, C. chlorinated isobutylene/isoprene copolymers, and D. blends of any of the above polymers A–C with either styrene/butadiene copolymers or natural rubber, the proportion of the polymer A, B or C being at least 50 weight percent of the blend;

the process comprising incorporating into polymer A, B, or C or polymer blend D, prior to vulcanization, about 0.5–5 parts per 100 parts by weight of polymer or polymer blends of at least one of the following esters:

1. bis(5-norbornene-2-methyl) phosphite,
2. tris(5-norbornene-2-methyl) phosphite, and
3. tris(5-norbornene-2-methyl) phosphate.

It has also been discovered that the same esters, used in the same amounts, improve the flex resistance of chloroprene copolymers with sulfur (B) and of their blends with either styrene/butadiene copolymers or natural rubber (D).

This invention further provides polymers and polymer blends having in their vulcanized state improved ozone resistance, and in some cases also improved flex resistance, said polymers and polymer blends being prepared by the above process.

DETAILED DESCRIPTION OF THE INVENTION

The phosphate and phosphites useful in the process of the present invention are described in the copending application, Ser. No. 698,017, of M. C. Chen, filed concurrently. They are rather difficult to isolate in their pure state regardless of the method by which they are made, a mixture of all three compounds, normally also containing some 5-norbornene-2-methanol, usually being obtained. For the purpose of the present invention, a mixture of all three esters is satisfactory, and isolation and purification of each individual ester is not required. Any free 5-norbornene-2-methanol present in the mixture is harmless. The relative proportion of each component of the mixture can be readily ascertained by known analytical techniques, especially by combining gas chromatography with mass spectrometry.

The most effective antiozonant among the above esters is tris(5-norbornene-2-methyl) phosphite. As the level of this compound in the mixture increases, the total amount of the mixture required to produce satisfactory ozone resistance decreases. For the best ozone protection without undesirable changes in other properties of the polymers, at the most reasonable cost, it is preferred to use about 1–3 parts of the ester or ester mixture per 100 parts by weight of polymer or polymer blend.

The homopolymers, copolymers, and polymer blends in which the antiozonants of this invention are used are well known in the art and either are commercially available or can be made or blended according to available patent literature or technical literature.

Representative monomers which can be copolymerized with chloroprene include vinyl aromatic compounds, such as styrene, the vinyltoluenes, and vinylnaphthalenes; aliphatic conjugated diolefin compounds such as 1,3-butadiene, isoprene, 2,3-dimethyl-1,3-butadiene, and 2,3-dichloro-1,3-butadiene; vinyl ethers, esters, and ketones, such as methyl vinyl ether, vinyl acetate, and methyl vinyl ketone; acrylic and methacrylic acids and their esters, amides, and nitriles such as ethyl acrylate, methyl methacrylate, methacrylamide, and acrylonitrile.

Normally, the phosphate and phosphites of the present invention will be added to standard vulcanication recipes of polymers. Standard vulcanization recipes for the chloroprene polymer and the blends are described in Murray and Thompson, *The Neoprenes*, E. I. du Pont de Nemours and Co., 1963, chapters III and V. The recipes normally include metal oxides, reinforcing agents and fillers, antioxidants, vulcanization agents such as sulfur, retarders and accelerators, plasticizers, etc. In recipes containing elemental sulfur, the level of sulfur preferably should not exceed about 4 parts 100 parts by weight of polymer because otherwise the antiozonant activity of the active ingredients is reduced. However, the amount of sulfur usually is below this level. Incorporation of the antiozonants into the polymer can be conveniently accomplished by blending with the polymer and any other ingredients of the recipe on a rubber mill, in a Banbury mixer, or in any other suitable mixing equipment.

It is also possible to add these esters to chloroprene polymer latex prior to the isolation of polymer therefrom. The polymer is isolated by standard techniques, such as freeze roll isolation followed by hot air drying.

The antiozonant effect of the compounds of this invention can be determined either in a static or in a dynamic test. Both tests expose cured elastomer samples to ozone in a test chamber at 40° C. For static exposures, samples of the vulcanizates, prepared as described in the following examples, 0.25 × 0.075 × 6 inches in dimension, mounted on varnished wooden racks, were subjected to the indicated tensile strains. The dynamic tests were carried out by the "roller" method described in Rubber Chemistry and Technology 32, 1119 (1959). The test pieces were flexed at a rate of 30 cycles per minute. The number of hours required to produce a given degree of cracking was observed.

The DeMattia flex resistance was measured by ASTM Method 813-59 (1970).

In the illustrative examples below, all parts, proportions, and percentages are by weight unless otherwise indicated.

TEST POLYMERS

Polymer A — a sulfur/chloroprene copolymer prepared by the procedure of Example 1 of U.S. Pat. No. 3,920,623, to A. A. Khan. The Mooney viscosity of the polymer is 55–65 (ASTM D-1646).

Polymer B — a sulfur/chloroprene copolymer sold as Neoprene GRT by E. I. du Pont de Nemours and Company, Inc., of Mooney viscosity 52. This copolymer does not contain antiozonants.

Polymer C — a polychloroprene sold as Neoprene W by E. I. du Pont de Nemours and Company, Inc., of Mooney viscosity 50. This polymer does not contain antiozonants.

Polymer D — a sulfur/chloroprene copolymer prepared by the procedure of Polymer A. Polymerization is stopped by adding an emulsion that contains 1.2 parts of Additive II (see below) based on unstripped emulsion solids in addition to the conventional ingredients. The unpolymerized monomer is removed, and latex is aged at pH 12.2 for 8 hours. The pH is adjusted to 5.6 with acetic acid, and the polymer is isolated on a freeze roll and subsequently hot air dried.

ACTIVE INGREDIENTS

ADDITIVE I

Phosphorous trichloride (68.5 g.) was dissolved in 100 ml. petroleum ether and cooled with dry ice. A solution of 5-norbornene-2-methanol (186 g.) and pyridine (119 g.) dissolved in 200 ml. petroleum ether was added dropwise with stirring to the PCl₃ solution. The addition was made at such a rate that the temperature of the exothermic reaction did not rise above 0° C. After completion of the addition, the mixture was stirred at room temperature for an hour. Pyridine hydrochloride was removed by filtration and the filtrate dried over potassium carbonate. Solvent was stripped under reduced pressure. The residue, a yellowish liquid, had the following gas chromatographic analysis (area %):

5-norbornene-2-methanol: 42%
bis(5-norbornene-2-methyl) phosphite: 17%
tris(5-norbornene-2-methyl) phosphite: 22%
tris(5-norbornene-2-methyl) phosphate: 15%

ADDITIVE II

A mixture of 0.3 g. sodium and 314 g. 5-norbornene-2-methanol was allowed to react at 80° C. for about 3 hours under a nitrogen atmosphere. The solution was cooled to room temperature, and 261.5 g. triphenyl phosphite was added. The reaction mixture was stirred at room temperature for about 15 hours under a nitrogen atmosphere. Removal of volatiles gave 331.0 g. of residue having the following composition, as determined by gas chromatography:

5-norbornene-2-methanol: 13.9 area %
bis(5-norbornene-2-methyl) phosphite: 29.5 area %
tris(5-norbornene-2-methyl) phosphite: 41.1 area %
tris(5-norbornene-2-methyl) phosphate: 3.3 area %

Small additional peaks due to unknown compounds also were observed.

ADDITIVE III

A mixture of 0.5 g. sodium and 1000 g. 5-norbornene-2-methanol was allowed to react at 80° C. for about 3 hours under a nitrogen atmosphere. The solution was cooled to about 50° C., and 686 g. triphenyl phosphite was added. After the addition, the mixture was heated at 100° C. for about 15 hours. Volatiles, consisting primarily of excess 5-norbornene-2-methanol and phenol, were removed under vacuum, and the resulting crude product, 864.3 g., was treated with 54 g. activated charcoal. The purified product, 815.6 g., was shown by gas chromatography to have the following composition:

5-norbornene-2-methanol: 5.8 area %
bis(5-norbornene-2-methyl) phosphite: 15.9 area %
tris(5-norbornene-2-methyl) phosphite: 65.5 area %
tris(5-norbornene-2-methyl phosphate: 0.7 area %

Small additional peaks were observed but not identified.

ADDITIVE IV

A mixture of 372 g. 5-norbornene-2-methanol and 303 g. triethylamine was slowly added with vigorous agitation to a solution of 206 g. phosphorus trichloride in 700 ml. benzene at 0° C. The addition was made at such a rate that the temperature of the reaction mixture did not exceed 2° C. The addition took 4 hours. The temperature of the reaction mixture was then raised to 25° C. and a further 193 g. 5-norbornene-2-methanol was added. After about 16 hours at room temperature, the reaction mixture was filtered, and the filtrate extracted with 250 ml. water and dried over sodium sulfate. After removal of volatiles, there was obtained 401.3 g. of product, which was vacuum distilled to give a fraction of b.p. 157°–160° C. (0.5 mm Hg). This fraction contained 8 area % 6-norbornene-2-methanol and 91% bis(5-norbornene-2-methyl) phosphite.

ADDITIVE V

5-Norbornene-2-methanol (186 g.), 130 g. pyridine, and 300 ml. benzene were added to a one-liter flask equipped with a reflux condenser protected by a calcium chloride drying tube, a mechanical stirrer, a dropping funnel, and a thermometer. The mixture was cooled to about 0° C. A solution of 76.5 g. phosphorus oxychloride in 50 ml. benzene was added dropwise with stirring over a period of 2 hours. The reaction mixture temperature was kept at 30° C. or less by external cooling. After the addition, the reaction mixture was stirred for 30 minutes at about 30° C. and then heated at reflux for 2 hours. After cooling, precipitated pyridine hydrochloride was removed by filtration, and the precipitate washed with 50 ml. benzene. The combined filtrate and washing were extracted twice with 250-ml. portions of cold water and then dried over anhydrous sodium sulfate. Solvent was removed under vacuum and the resulting product analyzed by gas chromatography.

The product had the following composition:

tris(5-norbornene-2-methyl) phosphate: 95.2 area %
5-norbornene-2-methanol: 0.42 area %
tris(5-norbornene-2-methyl) phosphite: 0.82 area %

In the following examples, polymer masterbatches were prepared as shown. In most cases, control samples without an additive of this invention were also tested.

EXAMPLE 1

| MASTERBATCH PREPARATION | Masterbatch 1 | Masterbatch 2 |
|---|---|---|
| Polymer A | 100 | — |
| Polymer B | — | 100 |
| Stearic Acid | 1.5 | 1.5 |
| Antidegradant[a] | 2 | 2 |
| Magnesia | 4 | 4 |
| General Purpose Furnace Black | 45 | 45 |
| Aromatic Oil[b] | 5 | 5 |
| Zinc Oxide | 5 | 5 |
| | 162.5 | 162.5 |

| FORMULATION AND TESTING | 1 | 2 | 3 | 4 |
|---|---|---|---|---|
| Masterbatch 1 | 162.5 | 162.5 | — | — |
| Masterbatch 2 | — | — | 162.5 | 162.5 |
| Additive I | — | 2 | — | 0.8 |
| Press Cure: 35 Min. at 153° C. | | | | |
| DeMattia Flex | | | | |
| (2¼" stroke; 0.08" pierced) | | | | |
| Original | | | | |
| Cut growth at 1.1 × 10⁶ flexes | 0.2 in. | 0 | — | — |
| 10³ flexes to 0.5 in. growth | >1100 | >1100 | 15.7 | 48 |
| Aged 3 Days at 250° F. | | | | |
| Cut growth at 1.26 × 10⁶ flexes | >0.5 in. | 0.02 in. | — | — |
| 10³ flexes to 0.5 in. growth | 596 | >1260 | <1.5 | 3.5 |

[a]Mixture of 65% n-phenyl-β-naphthylamine, 35% N,N'-diphenyl-para-phenylenediamine, sold as "Akroflex" CD, by E. I. du Pont de Nemours and Company
[b]Sold as "Sundex" 790, by Sun Oil Company

EXAMPLE 2

| MASTERBATCH PREPARATION | Masterbatch 3 |
|---|---|
| Polymer C | 100 |
| Stearic Acid | 0.5 |
| Magnesia | 4 |
| Semi-Reinforcing Carbon Black | 58 |
| Naphthenic Oil[a] | 10 |
| Antioxidant[b] | 2 |
| Zinc Oxide | 5 |
| 2-Mercapto-2-Imidazoline | 0.75 |
| Tetramethylthiuram Disulfide | 0.5 |
| | 180.75 |

| FORMULATION AND TESTING | 1 | 2 | 3 |
|---|---|---|---|
| Masterbatch 3 | 180.75 | 180.75 | 180.75 |
| Diaryl-p-phenylenediamine[c] | — | 2 | — |
| Additive I | — | — | 2 |
| Press Cure: 20 Min. at 153° C. | | | |
| Ozone Resistance (3 ppm at 40° C.) | | | |
| Dynamic | | | |
| Original | | | |
| Hrs. to Bad Cracking | 3 | 11 | 32 |
| Aged 3 Days at 121° C. | | | |
| Hrs. to Bad Cracking | 32 | 62 | 196 |
| Static (40% Elongation) | | | |
| Original | | | |
| Hrs. to Break | 13 | >300 | >300 |
| Aged 7 Days at 100° C. | | | |
| Hrs. to Break | 42 | 74 | >300 |

[a]Sold as "Circo" LP Oil, by Sun Oil Co.
[b]2,2'-Methylenebis(6-tert-butyl-p-cresol), sold as Antioxidant 2246, by American Cyanamid Co.
[c]Sold as "Akroflex" AZ, by E. I. du Pont de Nemours and Company

EXAMPLE 3

| FORMULATION AND TESTING | 1 | 2 | 3 | 4 | 5 | 6 |
|---|---|---|---|---|---|---|
| Masterbatch 1 | 162.5 | 162.5 | 162.5 | — | — | — |
| Masterbatch 2 | — | — | — | 162.5 | 162.5 | 162.5 |
| Antiozonant I[a] | — | 1 | — | — | 2 | — |
| Additive I | — | — | 1 | — | — | 2 |
| Stress-Strain Properties | | | | | | |
| (Press Cure 30 Minutes at 153° C.) | | | | | | |
| Hardness, Shore A | 66 | 64 | 60 | 70 | 66 | 64 |
| 100% Modulus, psi | 405 | 345 | 370 | 600 | 440 | 430 |
| Tensile Strength, psi | 3595 | 3445 | 3115 | 3400 | 3240 | 3115 |
| Elongation, % | 630 | 670 | 610 | 420 | 510 | 500 |
| DeMattia Flex | | | | | | |
| (2¼" stroke; 0.08" pierced) | | | | | | |
| Original | | | | | | |
| 10³ flexes to 0.5 in. growth | — | — | — | 29 | 220 | 472 |
| Cut growth at 1.06 × 10⁶ flexes | 0.18 in. | 0 | 0 | — | — | — |
| Aged 3 Days at 121° C. | | | | | | |
| 10³ flexes to 0.5 in. growth | 611 | >1310 | >1310 | <1.5 | 33.3 | 70 |
| Cut growth at 1.31 × 10⁶ flexes | >0.5 in. | 0.22 in. | 0.08 in. | — | — | — |
| Ozone Resistance | | | | | | |
| (3 ppm. at 40° C.) | | | | | | |
| Dynamic | | | | | | |
| Original | | | | | | |
| Hrs. to Bad Cracking | 39 | 39 | 47 | 31.5 | 61.5 | 91.5 |
| Aged 7 Days at 100° C. | | | | | | |
| Hrs. to Bad Cracking | 29.5 | 29.5 | 35 | 29.5 | 74.5 | 163.5 |

[a]Mixture of 5-norbornene-2-methyl succinate (25%), glutarate (50%), and adipate (25%)

EXAMPLE 4

| FORMULATION AND TESTING | 1 | 2 |
|---|---|---|
| Polymer D | — | 100 |
| Polymer A | 100 | — |
| Stearic Acid | 0.5 | 0.5 |
| Magnesia | 4 | 4 |
| N-Phenyl-α-Naphthylamine | 2 | 2 |
| General Purpose Furnace Black | 45 | 45 |
| Intermediate Super-Abrasion Carbon Black | 10 | 10 |
| Aromatic Oil[a] | 5 | 5 |
| Zinc Oxide | 5 | 5 |
| Additive II | 1.2 | [b] |
| Mooney Scorch (121° C.) | | |
| Minimum Value | 42 | 41 |
| Minutes to 2 Pt. Rise | 26 | >30 |
| Press Cure: 30 Min. at 153° C. | | |
| Ozone Resistance (3 ppm at 40° C.) | | |
| Aged 3.5 Months at 25° C. | | |
| Dynamic | | |
| Hrs. to Bad Cracking | 19 | 32 |
| Additional Aging 7 Days at 100° C. | | |
| Hrs. to Bad Cracking | 41 | 86 |

[a] Sold as "Sundex" 790, by Sun Oil Co.
[b] See polymer description.

EXAMPLE 5

| FORMULATION AND TESTING | 1 | 2 |
|---|---|---|
| Natural Rubber[a] | 50 | 50 |
| Polymer C | 50 | 50 |
| Naphthenic Oil[b] | 10 | 10 |
| Semi-Reinforcing Carbon Black | 30 | 30 |
| Stearic Acid | 2 | 2 |
| Zinc Oxide | 4 | 4 |
| N-Cyclohexyl-2-Benzothiazole Sulfenamide | 0.6 | 0.6 |
| Diphenylguanidine | 0.3 | 0.3 |
| Sulfur | 1.3 | 1.3 |
| Antioxidant[c] | 2 | 2 |
| Additive I | — | 2 |
| Press Cure: 15 Min. at 160° C. | | |
| Ozone Resistance (0.5 ppm at 40° C.) | | |
| Dynamic | | |
| Hrs. to Bad Cracking | 17 | 62 |
| Static | | |
| 20% Elongation, Hrs. to Break | 52 | >200 |
| 40% Elongation, Hrs. to Break | 21 | >200 |

[a] Natural Rubber RSS#1 Breakdown
[b] Sold as "Circo" LP, by Sun Oil Co.
[c] 2,2'-Methylenebis(6-t-butyl-p-cresol), sold as "Antioxidant" 2246, by American Cyanamid Co.

EXAMPLE 6

| FORMULATION AND TESTING | 1 | 2 | 3 |
|---|---|---|---|
| Polymer C | 50 | 50 | 50 |
| Styrene-Butadiene Copolymer[a] | 50 | 50 | 50 |
| Semi-Reinforcing Carbon Black | 30 | 30 | 30 |
| Naphthenic Oil | 10 | 10 | 10 |
| Stearic Acid | 2 | 2 | 2 |
| Antioxidant[b] | 2 | 2 | 2 |
| N-Cyclohexyl-2-Benzothiazole Sulfenamide | 0.6 | 0.6 | 0.6 |
| Diphenylguanidine | 0.3 | 0.3 | 0.3 |
| Sulfur | 1.3 | 1.3 | 1.3 |
| Zinc Oxide | 5 | 5 | 5 |
| Additive II | — | 2 | — |
| Additive III | — | — | 2 |
| Press Cure: 25 Min. at 177° C. | | | |
| Ozone Resistance (3 ppm at 40° C.) | | | |
| Dynamic | | | |
| Original | | | |
| Hrs. to Bad Cracking | 6 | 27 | 40 |
| Aged 7 Days at 100° C. | | | |
| Hrs. to Bad Cracking | 10.5 | 23.5 | 37.5 |
| Static (40% Elongation) | | | |
| Original | | | |
| Hrs. to Break | 28 | >170 | >170 |

[a] SBR 1502, from Phillips Petroleum Co.
[b] Octylated Diphenylamine, sold as "ANTOX" N, by E.I. du Pont de Nemours and Company

EXAMPLE 7

| FORMULATION AND TESTING | 1 | 2 | 3 |
|---|---|---|---|
| Polymer C | 100 | 100 | 100 |
| Titanium Dioxide[a] | 30 | 30 | 30 |
| Aluminum Silicate[b] | 30 | 30 | 30 |
| Stearic Acid | 2 | 2 | 2 |
| Magnesia | 4 | 4 | 4 |
| Zinc Oxide | 5 | 5 | 5 |
| Antiozonant I[c] | — | 2 | — |
| Additive II | — | — | 2 |
| Sulfur | 1 | 1 | 1 |
| Di-ortho-tolylguanidine | 1 | 1 | 1 |
| Tetramethylthiuram Monosulfide | 1 | 1 | 1 |
| Press Cure: 30 Min. at 153° C. | | | |
| Ozone Resistance (3 ppm at 40° C.) | | | |
| Dynamic | | | |
| Original | | | |
| Hrs. to Bad Cracking | 14 | 22 | 45 |
| Aged 7 Days at 100° C. | | | |
| Hrs. to Bad Cracking | 21.5 | 27.5 | 83.5 |
| Static (40% Elongation) | | | |
| Original | | | |
| Hrs. to Break | 18 | 27.5 | >128.5 |

[a] "Ti-Pure" 902, from E.I. du Pont de Nemours and Company
[b] "Optiwhite" Clay, from E.W. Kauffman Co.
[c] Mixture of 5-norbornene-2-methyl succinate (25%), glutarate (50%), and adipate (25%)

EXAMPLE 8

| FORMULATION AND TESTING | 1 | 2 | 3 | 4 |
|---|---|---|---|---|
| Chlorinated Isobutylene-Isoprene Copolymer[a] | 50 | 50 | 50 | 50 |
| Pale Crepe Natural Rubber | 50 | 50 | — | — |
| Styrene-Butadiene Copolymer[b] | — | — | 50 | 50 |
| Titanium Dioxide | 35 | 35 | 35 | 35 |
| Aluminum Silicate[c] | 40 | 40 | 40 | 40 |
| Stearic Acid | 1 | 1 | 1 | 1 |
| Additive II | — | 2 | — | 2 |
| Zinc Oxide | 5 | 5 | 5 | 5 |
| Sulfur | 0.7 | 0.7 | 0.7 | 0.7 |
| 2,2'-Benzothiazyl Disulfide | 0.75 | 0.75 | 0.75 | 0.75 |
| Alkyl Phenol Disulfide[d] | 1.25 | 1.25 | 1.25 | 1.25 |
| Press Cure: 30 Min. at 153° C. | | | | |
| Stress-Strain Properties | | | | |
| Hardness, A | 47 | 39 | 46 | 41 |
| 100% Modulus, psi | 180 | 110 | 150 | 110 |
| Tensile Strength, psi | 2020 | 2020 | 1880 | 960 |
| Elongation, % | 540 | 640 | 930 | 910 |
| Ozone Resistance (3 ppm at 40° C.) | | | | |
| Dynamic | | | | |
| Hrs. to Bad Cracking | 11 | >122.5 | 32.5 | >122.5 |
| Static - 40% Elongation | | | | |
| Hrs. to Break | 67.5 | >72 | 20.5 | >72 |

[a] Butyl HT-1068, from Exxon Chemicals Co.
[b] SBR 1502, from Phillips Petroleum Co.
[c] Chemically modified aluminum silicate, sold as "Nucap" 290, by J.M. Huber Co.
[d] Sold as "Vultac" 5, by Pennwalt Co.

EXAMPLE 9

| MASTERBATCH PREPARATION | Masterbatch 4 |
|---|---|
| Polymer C | 50 |
| Pale Crepe Natural Rubber | 50 |
| Semi-Reinforcing Carbon Black | 30 |
| Naphthenic Oil[a] | 10 |
| Stearic Acid | 2 |
| Antioxidant[b] | 2 |
| Zinc Oxide | 5 |
| N-Cyclohexyl-2-Benzothiazyl Sulphenamide[c] | 0.6 |
| Diphenylguanidine | 0.3 |
| Sulfur | 1.3 |
| | 151.2 |

| FORMULATION AND TESTING | 1 | 2 | 3 | 4 |
|---|---|---|---|---|
| Masterbatch 4 | 151.2 | 151.2 | 151.2 | 151.2 |
| Additive | none | IV | V | III |
| Parts | — | 2.4 | 2.28 | 2 |
| Norbornene Content (Parts) | — | 1.55 | 1.47 | 1.21 |
| Press Cure: 30 Min. at 153° C. | | | | |
| Stress-Strain Properties | | | | |
| Shore A Hardness | 42 | 36 | 37 | 37 |
| 300% Modulus, psi | 640 | 500 | 440 | 495 |
| Tensile Strength, psi | 2190 | 1480 | 1760 | 1610 |
| Elongation, % | 580 | 540 | 640 | 555 |
| Ozone Resistance | | | | |
| Static (40% Elongation), 3 ppm at 40° C. | | | | |
| Original (Hrs. to Break) | 43.5 | >127 | >127 | >127 |
| Aged 7 Days at 100° C. (Hrs. to Break) | 37.5 | >232 | >232 | >232 |
| Dynamic (0.5 ppm at 40° C.) | | | | |
| Original (Hrs. to Bad Cracking) | 41 | 96 | 54 | 96 |
| Aged 7 Days at 100° C. (Hrs. to Bad Cracking) | 13 | 39.5 | 95.5 | >95.5 |

[a]Sold as "Circo" LP Oil, by Sun Oil Co.
[b]Octylated Diphenylamine, sold as "ANTOX" N, by E.I. du Pont de Nemours and Company
[c]Sold as "Conac" S, by E.I. du Pont de Nemours and Company

EXAMPLE 10

| | |
|---|---|
| Polymer C | 70 |
| Styrene-Butadiene Copolymer[a] | 30 |
| Stearic Acid | 1 |
| Medium Thermal Black | 85 |
| Fast Extruding Furnace Black | 15 |
| Aromatic Oil[b] | 20 |
| Polyethylene Processing Aid | 2 |
| Magnesia | 2 |
| Dinitrosopentamethylenetetramine | 10 |
| Zinc Oxide | 5 |
| Pentaerythritol | 5 |
| 2-Mercapto-2-Imidazoline | 2 |
| Diethylthiourea | 2 |
| Sulfur | 1 |
| Octylated Diphenylamine[c] | 1.5 |
| Antiozonant | As Indicated |

[a]SBR 1502, from Phillips Petroleum Co.
[b]Sold as "Sundex" 790, by Sun Oil Co.
[c]Sold as "Octamine", by Uniroyal Co.

The rubber compound was extruded through a 1" × ¼" die using a 2" diameter Royal extruder. The extruded rubber compound was placed in a hot air oven at 191° C. for 8 minutes. The resultant cured product was a closed cell sponge.
Ozone Resistance of Looped Test Specimens (ASTM D-518, Procedure B) (0.5 ppm Ozone) Rating 10 = no attack; Rating 0 = very severe attack (failure)

| | 1 | 2 | 3 | 4 | 5 |
|---|---|---|---|---|---|
| Additive II | 0.3 | 0.6 | — | — | — |
| Arylamine Antiozonant[a] | — | — | 0.6 | 1.2 | — |

[a]50% N-phenyl-β-naphthyl amine; 50% diaryl-p-phenylene diamine, sold as "Akroflex" DAZ, by E.I. du Pont de Nemours and Company

| Hours Exposed | Rating | | | | |
|---|---|---|---|---|---|
| 24 | 10 | 10 | 10 | 10 | 10 |
| 48 | 10 | 10 | 10 | 10 | 8 |
| 96 | 10 | 10 | 8 | 10 | 5 |
| 475 | 10 | 10 | 6 | 10 | 0 |

I claim:

1. A process for improving the ozone resistance of vulcanized:
   A. chloroprene polymers containing about 90-100 weight percent chloroprene and 0-10 weight percent of a copolymerizable organic monomer,
   B. chloroprene/sulfur copolymers in which the organic monomer composition is about 90-100 weight percent chloroprene and 0-10 weight percent of a copolymerizable monomer,
   C. chlorinated isobutylene/isoprene copolymers, and
   D. blends of any of the above polymers A-C with either styrene/butadiene copolymers or natural rubber, the proportion of the polymer A, B or C being at least 50 weight percent of the blend;
   said process comprising incorporating into the polymer or polymer blend prior to vulcanization about 0.5-5 parts per 100 parts by weight of polymer or polymer blend of at least one of the following esters:
   (1) bis(5-norbornene-2-methyl) phosphite,
   (2) tris(5-norbornene-2-methyl) phosphite, and
   (3) tris(5-norbornene-2-methyl) phosphate.

2. The process of claim 1 wherein a mixture of all three esters is used.

3. The process of claim 2 wherein tris(5-norbornene-2-methyl) phosphite predominates.

4. The process of claim 1 wherein the ester is bis(5-norbornene-2-methyl) phosphite.

5. The process of claim 1 wherein the ester is tris(5-norbornene-2-methyl) phosphate.

6. The process of claim 1 wherein the polymer is a chloroprene polymer or a chloroprene/sulfur copolymer.

7. The process of claim 6 wherein the copolymer is a chloroprene/sulfur copolymer.

8. The process of claim 1 wherein the esters are blended with unvulcanized polymer stocks.

9. The process of claim 1 wherein the polymer is a chloroprene polymer, and the esters are added to polymer latex prior to the isolation of polymer therefrom.

10. The process of claim 1 wherein the proportion of the ester or ester mixture is about 1-3 parts per 100 parts by weight of polymer or polymer blend.

11. An unvulcanized composition of a polymer or polymer blend selected from:
   A. chloroprene polymers containing about 90-100 weight percent chloroprene and 0-10 weight percent of a copolymerizable organic monomer,
   B. chloroprene/sulfur copolymers in which the organic monomer composition is about 90-100 weight percent chloroprene and 0–10 weight percent of a copolymerizable monomer,
C. chlorinated isobutylene/isoprene copolymers, and
D. blends of any of the above polymers A-C with styrene/butadiene copolymers or with natural rubber, the proportion of the polymer A, B, or C being at least 50 weight percent of the blend;
  said composition comprising about 0.5–5 parts per 100 parts by weight of polymer or polymer blend of at least one of the following esters:
  (1) bis(5-norbornene-2-methyl) phosphite,
  (2) tris(5-norbornene-2-methyl) phosphite, and
  (3) tris(5-norbornene-2-methyl) phosphate.

12. A vulcanized product obtained by the vulcanization of a composition of claim 11.

13. A composition of claim 11 wherein the polymer is a chloroprene polymer of chloroprene/sulfur copolymer.

14. A composition of claim 11 wherein a mixture of all three esters is used.

15. A composition of claim 14 wherein tris(5-norbornene-2-methyl) phosphite predominates.

16. A composition of claim 11 wherein the proportion of the ester or ester mixture is about 1–3 parts per 100 parts by weight of polymer or polymer blend.

17. A process for improving the flex resistance of vulcanized chloroprene/sulfur copolymers and of blends of chloroprene/sulfur copolymers with styrene/butadiene copolymers or with natural rubber, the organic monomer composition of said chloroprene/sulfur copolymers being about 90–100 weight percent chloroprene and 0–10 weight percent of a copolymerizable monomer, and the proportion of chloroprene/sulfur polymer in the blends being at least 50 weight percent of the blend;
  said process comprising incorporating into the chloroprene/sulfur copolymer or into the blend, prior to vulcanization, about 0.5–5 parts per 100 parts by weight of copolymer or polymer blend of at least one of the following esters:
  (1) bis(5-norbornene-2-methyl) phosphite,
  (2) tris(5-norbornene-2-methyl) phosphite, and
  (3) tris(5-norbornene-2-methyl) phosphate.

18. The process of claim 17 wherein a mixture of all three esters is used.

19. The process of claim 18 wherein tris(5-norbornene-2-methyl) phosphite predominates.

* * * * *